United States Patent [19]

van Eykern

[11] 4,248,240

[45] Feb. 3, 1981

[54] APPARATUS FOR DETECTING THE ACTIVITY OF THE RESPIRATORY ORGANS AND THE HEART OF A LIVING BEING

[75] Inventor: Leo A. van Eykern, Zuidhorn, Netherlands

[73] Assignee: Rijksuniversiteit te Groningen, Netherlands

[21] Appl. No.: 22,189

[22] Filed: Mar. 20, 1979

[30] Foreign Application Priority Data

Mar. 20, 1978 [NL] Netherlands ......................... 7803017

[51] Int. Cl.³ .............................................. A61B 5/04
[52] U.S. Cl. .................................... 128/671; 128/708
[58] Field of Search ............... 128/671, 696, 700, 703, 128/708, 709, 710, 721, 722, 733

[56] References Cited

U.S. PATENT DOCUMENTS

| 3,483,861 | 12/1969 | Tiep | 128/721 |
|---|---|---|---|
| 3,572,317 | 3/1971 | Wade | 128/671 |
| 3,822,696 | 7/1974 | Ekstrom et al. | 128/703 |
| 3,871,360 | 3/1975 | Van Horn et al. | 128/671 |
| 4,031,884 | 6/1977 | Henzel | 128/671 |

Primary Examiner—William E. Kamm
Attorney, Agent, or Firm—Holman & Stern

[57] ABSTRACT

Apparatus for detecting the activity of the respiratory organs and the heart of a living being, using passive measuring electrodes applied to the surface of the skin. The apparatus comprises a pair of paths having a common input for receiving respiratory EMG signals. The path serving for detection of respiratory activity includes a gating member controlled by gating signals from the path serving for the detection of cardiac activity.

7 Claims, 1 Drawing Figure

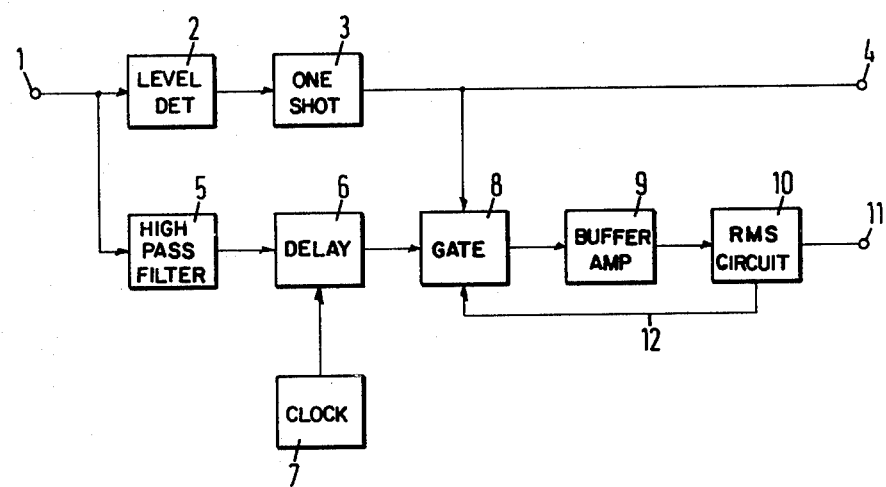

APPARATUS FOR DETECTING THE ACTIVITY OF THE RESPIRATORY ORGANS AND THE HEART OF A LIVING BEING

Various proposals have been made for measuring the activity of the respiratory organs of a living being. Thus the activity has been measured by determing the current of respiratory air or the change in volume of the respiratory organs.

It turns out that these two methods do not give measuring results regarding the activity referred to, which are satisfactory under all conditions.

It is an object of the present invention to determine this activity by different means. In it, use is made of the electromyogram of the respiratory muscles, and this mainly the electromyogram of the diaphragm. For, generally speaking, the diaphragm can be regarded as the main motor of respiration, and especially during inspiration.

It has been found that when the electromyogram of the diaphragm is taken by, for example, applying a pair of electrodes left and right of the sternum just below the rib curve, the electromyogram of the diaphragm is considerably affected by interference from the electrical activity of the heart during the contraction of the heart muscle. Where these cardiac pulses have an intensity many times greater than that of the electromyogram of the diaphragm, the interference is very intense.

The invention contemplates making a distinction between the electrical activity of the diaphragm and that of the cardiac pulses, thereby making it possible not only to measure the muscle activity needed for inspiration, but also to measure the cardiac pulses.

In particular, as regards the muscular activity needed for inspiration, so long as there is respiration, the breathing frequency can be determined. Moreover, it can be derived from the intensity whether, and to what extent, breathing is impeded by an obstruction in the respiratory tract.

As regards the cardiac pulses, from these, so long as the heart is active, for example, the frequency can be determined.

In order to obtain such a separation of the cardiac pulses and the diaphragm electrical activity, use is made of apparatus which, according to the invention, comprises a pair of paths having a common input adapted to receive respiratory electromyogram signals, or EMG signals for short, and in which the path serving for detection of respiratory activity includes a gating member controlled by gating pulses from the path serving for the detection of cardiac activity.

In this way it is possible to measure not only the muscular activity needed for inspiration, but also to measure the cardiac pulses, without these two affecting one another.

One embodiment of the apparatus according to the invention will now be described, by way of example, with reference to the accompanying drawing, showing a schematic diagram of the same.

As shown in the drawing, the apparatus comprises an input terminal 1 to which an EMG signal is to be applied. Extending from terminal 1 are two paths, one to an output terminal 4 and one to an output terminal 11.

The path extending to output terminal 4 serves for the cardiac detection, and comprises, in series, a comparator 2 and a standardizer 3.

When the cardiac QRS complex present in the EMG signal passes a pre-determined level in comparator 2, the polarity of the output signal from comparator 2 is reversed. This change in polarity is standardized in standardizer 3 which, for example, may be a one short or monostable multivibrator, to a pulse having a length of 100 msec, that is to say, a length 10% greater than the duration of the QRS complex. This standardized cardiac signal is then supplied as the cardiac signal to the output terminal 4 of the cardiac detection path.

The other path, extending from input terminal 1 to output terminal 11, serves for detecting respiratory activity.

As viewed from input terminal 1, this path includes, in series, a highpass filter 5, a delay device 6, a gating device 8, a buffer or matching amplifier 9, and a device for determining the effective value 10. The EMG signal supplied to terminal 1 is first passed through the Rms or highpass filter with, for example, a frequency of 60 Hz, and then delayed in time in device 6. This time delay can be obtained by means of a so-called bucket memory, the delay time of which is determined by a clock generator 7. The delay time introduced by delay device 6 is, for example, approximately 5 milliseconds, with a maximum of 50 milliseconds. The delayed EMG signal, which comprises both the cardiac signal and the respiratory EMG signal, is then supplied to gating device 8.

Extending from standardizer 3 in the cardiac detection path is also a connection to the control input of gating device 8. This serves for the control of gating device 8 by the output signal of standardizer 3. In particular, during the period of the standardized cardiac signal passed through standardizer 3, the QRS signal in the delayed EMG signal from delay device 6 and supplied to gating device 8 is blocked.

The delay which the EMG signal undergoes in the delay device 6 is applied in order that the whole QRS complex may be blocked, that is to say, including that portion of the QRS complex which is present before the moment when the comparator 2 has detected the presence of the QRS complex.

The output signal from gating device 8 is not passed through a matching or buffer amplifier 9 to a device 10, in which the effective or root-mean-square (Rms) value of the respiratory EMG is determined, namely in a moving window with moving interval T approximately equal to 350 msec.

In order to fill up the voids arising from the blocking of the QRS complex in the EMG signal, a portion of the Rms or effective-value signal from device 10 can be fed-back from this device 10 to gating device 8.

The output signal from device 10 is finally passed to the output terminal 11 of the respiratory detection path.

It is clear that suitable measuring apparatus can be connected to the terminals 4 and 11 of the two paths.

The above will show that, according to the invention, in essence the activity of the basal inspiratory muscle for inspiration is measured by passive means, whereby the apparatus for performing this measurement comprises a small number of parts only.

Practice has shown that excellent results are obtained by means of the apparatus according to the invention, that is to say, both cardiac activity and the activity of the respiratory organs can be accurately measured without mutual influencing.

I claim:

1. Apparatus for detecting the activity of the respiratory organs and heart of a living being using passive measuring electrodes applied to the surface of the skin for detecting a composite EMG signal including respiratory electromyogram signals intermixed with QRS-complex signals, said apparatus comprising:

means for receiving said composite signal;

first signal path means connected to said means for receiving or providing a series of gating pulses corresponding to respective QRS-complex signals in the receiving composite signal;

second signal path means connected to said means for receiving;

gating means in said second signal path means and responsive to said gating pulses for blocking passage of said composite signal along said second signal path means during the period of each gating pulse; and output means disposed beyond said gating means in said second path means for providing a first output signal representative of respiratory organ activity.

2. The apparatus according to claim 1 wherein said first signal path means includes means responsive to each QRS-complex signal for providing each said gating pulses, respectively, at standardized amplitude and period.

3. The apparatus according to claim 1 or 2 wherein said second signal path means includes RMS circuit means for determining the RMS value of the amplitude of said first output signal disposed between said gating means and said output means and providing an RMS signal representative of said RMS value; and wherein said gating means includes means for passing said RMS signal in place of the blocked composite signal during the period of each of said pulses.

4. The apparatus according to claim 3 further comprising delay means disposed in said first signal path means in advance of said gating means for providing a delay interval to assure that the entire portion of the QRS-complex signal in said second signal path means is blocked during the period of said gating pulses.

5. The apparatus according to claim 4 further comprising control means for the delay interval of said delay means.

6. The apparatus according to claim 5 wherein said delay means includes a bucket memory and wherein said control means comprises a clock generator for delivering clock pulses to said bucket memory to control the rate of signal passage through the bucket memory.

7. The apparatus according to claim 1 further comprising delay means disposed in said first signal path means in advance of said gating means for providing a delay interval to assure that the entire portion of the QRS-complex signal in said second signal path means is blocked during the period of said gating pulses.

* * * * *

UNITED STATES PATENT AND TRADEMARK OFFICE
CERTIFICATE OF CORRECTION

PATENT NO. : 4,248,240
DATED : February 3, 1981
INVENTOR(S) : Leo A. van Eykern

It is certified that error appears in the above-identified patent and that said Letters Patent are hereby corrected as shown below:

Column 2, line 5, "short" should read --shot--

Column 2, line 18, DELETE "Rms or"

Column 2, line 42, "not" should read --next--

Column 3, line 7, "or" should read --for--

Column 4, lin3 7, "first" should read --second--

Signed and Sealed this

Eighth Day of December 1981

[SEAL]

Attest:

GERALD J. MOSSINGHOFF

Attesting Officer   Commissioner of Patents and Trademarks